US007908156B2

(12) United States Patent
Gore et al.

(10) Patent No.: US 7,908,156 B2
(45) Date of Patent: Mar. 15, 2011

(54) METHOD OF CALCULATING A PREMIUM PAYABLE BY AN INSURED PERSON ON A LIFE INSURANCE POLICY

(75) Inventors: Adrian Gore, Sandton (ZA); Herschel Phillip Mayers, Johannesburg (ZA)

(73) Assignee: Discovery Holdings Limited, Pretoria (ZA)

( * ) Notice: Subject to any disclaimer, the term of this patent is extended or adjusted under 35 U.S.C. 154(b) by 1516 days.

(21) Appl. No.: 10/251,120

(22) Filed: Sep. 20, 2002

(65) Prior Publication Data

US 2004/0059608 A1    Mar. 25, 2004

(51) Int. Cl.
*G06Q 40/00* (2006.01)

(52) U.S. Cl. ............... 705/4; 705/36 R; 705/35; 705/3; 705/38; 717/143; 600/300; 434/107

(58) Field of Classification Search ................ 705/3, 4, 705/36 R, 38; 600/300; 434/107
See application file for complete search history.

(56) References Cited

U.S. PATENT DOCUMENTS

| 4,556,216 A | | 12/1985 | Pitkanen |
| 4,699,375 A | | 10/1987 | Appelbaum et al. |
| 4,831,526 A | * | 5/1989 | Luchs et al. ............ 705/4 |
| 4,837,693 A | * | 6/1989 | Schotz .................. 705/4 |
| 4,860,275 A | | 8/1989 | Kakinuma et al. |
| 4,975,840 A | * | 12/1990 | DeTore et al. .......... 705/4 |
| 5,062,645 A | | 11/1991 | Goodman et al. |
| 5,136,502 A | | 8/1992 | Van Remortel et al. |
| 5,301,105 A | | 4/1994 | Cummings, Jr. |
| 5,324,077 A | | 6/1994 | Kessler et al. |
| 5,429,506 A | * | 7/1995 | Brophy et al. .......... 434/107 |
| 5,490,260 A | | 2/1996 | Miller et al. |
| 5,542,420 A | | 8/1996 | Goldman et al. |
| 5,549,117 A | | 8/1996 | Tacklind et al. |
| 5,550,734 A | | 8/1996 | Tarter et al. |
| 5,574,803 A | | 11/1996 | Gaborski et al. |
| 5,631,828 A | | 5/1997 | Hagan |
| 5,655,085 A | * | 8/1997 | Ryan et al. ............. 705/4 |
| 5,655,997 A | | 8/1997 | Greenberg et al. |
| 5,692,501 A | | 12/1997 | Minturn |
| 5,722,418 A | | 3/1998 | Bro |
| 5,745,893 A | | 4/1998 | Hill et al. |
| 5,752,236 A | * | 5/1998 | Sexton et al. .......... 705/4 |
| 5,774,883 A | * | 6/1998 | Andersen et al. ....... 705/38 |
| 5,832,467 A | | 11/1998 | Wavish |
| 5,867,821 A | | 2/1999 | Ballantyne et al. |
| 5,890,129 A | | 3/1999 | Spurgeon |
| 5,933,809 A | | 8/1999 | Hunt et al. |
| 5,933,815 A | | 8/1999 | Golden |
| 5,937,387 A | | 8/1999 | Summerell et al. |
| 5,987,434 A | * | 11/1999 | Libman ............... 705/36 R |
| 5,991,744 A | | 11/1999 | Dicrese |
| 6,039,688 A | * | 3/2000 | Douglas et al. ........ 600/300 |
| 6,049,772 A | | 4/2000 | Payne et al. |
| 6,085,174 A | | 7/2000 | Edelman |
| 6,085,976 A | | 7/2000 | Sehr |
| 6,108,641 A | | 8/2000 | Kenna et al. |
| 6,112,986 A | | 9/2000 | Berger et al. |
| 6,151,586 A | | 11/2000 | Brown |
| 6,169,770 B1 | | 1/2001 | Gamble et al. |
| 6,230,142 B1 | * | 5/2001 | Benigno et al. ........ 705/3 |
| 6,385,589 B1 | | 5/2002 | Trusheim et al. |
| 6,513,532 B2 | | 2/2003 | Mault et al. |
| 6,587,829 B1 | | 7/2003 | Camarda et al. |
| 6,602,469 B1 | | 8/2003 | Maus et al. |
| 6,611,815 B1 | | 8/2003 | Lewis et al. |
| 7,319,970 B1 | | 1/2008 | Simone |
| 7,380,707 B1 | | 6/2008 | Fredman |
| 7,383,223 B1 | | 6/2008 | Dilip et al. |
| 7,624,032 B2 | | 1/2009 | Radson |
| 7,685,007 B1 | | 3/2010 | Jacobson |
| 2001/0037275 A1 | | 11/2001 | Raskin et al. |
| 2002/0002495 A1 | | 1/2002 | Ullman |
| 2002/0013717 A1 | | 1/2002 | Ando et al. |
| 2002/0029158 A1 | * | 3/2002 | Wolff et al. .......... 705/4 |
| 2002/0035486 A1 | | 3/2002 | Huyn et al. |
| 2002/0038310 A1 | | 3/2002 | Reitberg |
| 2002/0049617 A1 | | 4/2002 | Lencki et al. |
| 2002/0055859 A1 | | 5/2002 | Goodman et al. |
| 2002/0087364 A1 | * | 7/2002 | Lerner et al. ........ 705/4 |
| 2002/0016231 A1 | | 8/2002 | Hele et al. |
| 2002/0103678 A1 | * | 8/2002 | Burkhalter et al. .... 705/4 |
| 2002/0111827 A1 | | 8/2002 | Levin et al. |
| 2002/0116231 A1 | * | 8/2002 | Hele et al. ........... 705/4 |
| 2002/0138309 A1 | | 9/2002 | Thomas |
| 2002/0152097 A1 | | 10/2002 | Javors |
| 2003/0009355 A1 | | 1/2003 | Gupta |
| 2003/0028483 A1 | | 2/2003 | Sanders et al. |

(Continued)

FOREIGN PATENT DOCUMENTS

| AU | 2001/276596 | 3/2003 |
| AU | 2005/323847 | 2/2007 |
| AU | 2007/257457 | 1/2009 |
| AU | 2007/257458 | 1/2009 |
| AU | 2007/257546 | 1/2009 |
| AU | 2007/298514 | 2/2009 |
| AU | 20071301521 | 5/2009 |
| CN | 2005/880047059 | 7/2007 |
| EP | 1050821 | 11/2000 |
| IL | 195735 | 12/2008 |
| IL | 195737 | 12/2008 |

(Continued)

OTHER PUBLICATIONS

Dialog Search history.*
U.S. Appl. No. 09/876,311, filed Jun. 7, 2001.
U.S. Appl. No. 09/876,311, Final Rejection Oct. 23, 2006.
U.S. Appl. No. 09/876,311, Final Rejection Dec. 16, 2009.
U.S. Appl. No. 09/876,311, Non-Final Rejection Jan. 17, 2006.

(Continued)

*Primary Examiner* — Dilek B Cobanoglu
(74) *Attorney, Agent, or Firm* — Fleit Gibbons Gutman Bongini & Bianco, PL; Paul D. Bianco; Martin Fleit

(57) ABSTRACT

A method of calculating a premium payable by an insured person on a life insurance policy uses the amount of claims made from a health insurance plan of the insured person and information regarding the general well-being and/or lifestyle of the insured person to calculate the premium payable. The premium is calculated using a base percentage amount which is then either increased or decreased. If the insured person has made few claims to the health insurance plan and they have taken positive steps to look after their health, they will be rewarded by a relatively lower premium on their life insurance policy.

8 Claims, No Drawings

U.S. PATENT DOCUMENTS

| | | | |
|---|---|---|---|
| 2003/0120521 A1* | 6/2003 | Sherman | 705/4 |
| 2003/0149596 A1 | 8/2003 | Bost | |
| 2003/0200142 A1 | 10/2003 | Hicks et al. | |
| 2003/0233278 A1 | 12/2003 | Thaddeus | |
| 2004/0030625 A1 | 2/2004 | Rabson et al. | |
| 2004/0059608 A1 | 3/2004 | Gore et al. | |
| 2004/0088219 A1 | 5/2004 | Sanders et al. | |
| 2004/0267570 A1 | 12/2004 | Becker et al. | |
| 2005/0033609 A1 | 2/2005 | Yang | |
| 2005/0038679 A1 | 2/2005 | Short | |
| 2005/0102172 A1 | 5/2005 | Sirmans, Jr. | |
| 2005/0131742 A1 | 6/2005 | Hoffman et al. | |
| 2005/0222877 A1 | 10/2005 | Radson et al. | |
| 2005/0222878 A1 | 10/2005 | Radson et al. | |
| 2005/0228692 A1 | 10/2005 | Hodgdon | |
| 2005/0234742 A1 | 10/2005 | Hodgdon | |
| 2005/0240449 A1 | 10/2005 | Radson et al. | |
| 2005/0256748 A1 | 11/2005 | Gore et al. | |
| 2006/0041454 A1 | 2/2006 | Matisonn et al. | |
| 2006/0064320 A1 | 3/2006 | Postrel | |
| 2006/0074801 A1 | 4/2006 | Pollard et al. | |
| 2006/0129436 A1 | 6/2006 | Short | |
| 2006/0218011 A1 | 9/2006 | Walker et al. | |
| 2007/0050217 A1 | 3/2007 | Holden, Jr. | |
| 2007/0233512 A1 | 10/2007 | Gore | |
| 2008/0154650 A1 | 6/2008 | Matisonn et al. | |
| 2008/0189141 A1 | 8/2008 | Gore et al. | |
| 2008/0197185 A1 | 10/2008 | Cronin et al. | |
| 2008/0255979 A1 | 10/2008 | Slutzky et al. | |
| 2009/0076903 A1 | 3/2009 | Schwarzberg et al. | |
| 2009/0150192 A1 | 6/2009 | Gore et al. | |
| 2009/0198525 A1 | 8/2009 | Gore et al. | |
| 2009/0240532 A1 | 9/2009 | Gore et al. | |
| 2009/0259497 A1 | 10/2009 | Gore et al. | |
| 2009/0265183 A1 | 10/2009 | Pollard et al. | |
| 2009/0299773 A1 | 12/2009 | Gore et al. | |
| 2009/0299774 A1 | 12/2009 | Gore et al. | |
| 2009/0299775 A1 | 12/2009 | Gore et al. | |
| 2009/0299776 A1 | 12/2009 | Gore et al. | |
| 2009/0307015 A1 | 12/2009 | Gore et al. | |
| 2010/0023354 A1 | 1/2010 | Gore et al. | |
| 2010/0023384 A1 | 1/2010 | Pollard et al. | |
| 2010/0049541 A1 | 2/2010 | Pollard et al. | |

FOREIGN PATENT DOCUMENTS

| | | |
|---|---|---|
| IL | 195738 | 12/2008 |
| WO | 02/47074 | 6/2002 |
| WO | 03/007230 | 1/2003 |
| WO | 2007/141695 | 12/2007 |
| WO | 2007/141696 | 12/2007 |
| WO | 2007/141968 | 12/2007 |
| WO | 2008/035280 | 3/2008 |
| ZA | 98/02005 | 3/1998 |
| ZA | 98/11943 | 12/1998 |
| ZA | 2000/04682 | 9/2000 |
| ZA | 2004/02587 | 4/2004 |
| ZA | 2004/02891 | 4/2004 |
| ZA | 2004/05935 | 7/2004 |
| ZA | 2004/06294 | 8/2004 |
| ZA | 2006/01934 | 3/2006 |
| ZA | 2006/04673 | 6/2006 |
| ZA | 2006/04674 | 6/2006 |
| ZA | 2006/04687 | 6/2006 |
| ZA | 2006/04688 | 6/2006 |
| ZA | 2006/07789 | 9/2006 |
| ZA | 2006/07992 | 9/2006 |
| ZA | 2008-03529 | 4/2008 |
| ZA | 2008/04807 | 6/2008 |
| ZA | 2008/04808 | 6/2008 |
| ZA | 2008/04809 | 6/2008 |
| ZA | 2008/04810 | 6/2008 |
| ZA | 2008/04811 | 6/2008 |
| ZA | 2009/01740 | 3/2009 |

OTHER PUBLICATIONS

U.S. Appl. No. 09/876,311, Non-Final Rejection Nov. 30, 2007.
U.S. Appl. No. 09/876,311, Non-Final Rejection Jul. 9, 2010.
U.S. Appl. No. 09/876,311, Requirement for Restriction May 18, 2007.
U.S. Appl. No. 09/876,311, Requirement for Restriction Jan. 2, 2009.
U.S. Appl. No. 09/876,311, Requirement for Restriction Jan. 16, 2009.
U.S. Appl. No. 09/876,311, Requirement for Restriction Aug. 10, 2009.
U.S. Appl. No. 09/876,311, Response to Office Action Jul. 19, 2006.
U.S. Appl. No. 09/876,311, Response to Office Action Feb. 23, 2007.
U.S. Appl. No. 09/876,311, Response to Office Action Jul. 17, 2007.
U.S. Appl. No. 09/876,311, Response to Office Action May 29, 2008.
U.S. Appl. No. 09/876,311, Response to Office Action Oct. 15, 2008.
U.S. Appl. No. 10/344,176, Response to Office Action Nov. 9, 2009.
U.S. Appl. No. 11/189,647, filed Jul. 26, 2005.
U.S. Appl. No. 11/189,647, Final Rejection May 11, 2010.
U.S. Appl. No. 11/189,647, Non-Final Rejection Aug. 14, 2009.
U.S. Appl. No. 11/189,647, Response to Office Action Feb. 15, 2010.
U.S. Appl. No. 10/819,256, filed Apr. 6, 2004.
U.S. Appl. No. 10/819,256, Final Rejection Jan. 6, 2009.
U.S. Appl. No. 10/819,256, Non-Final Rejection Mar. 18, 2008.
U.S. Appl. No. 10/819,256, Response to Office Action Sep. 18, 2008.
U.S. Appl. No. 11/097,947, filed Apr. 1, 2006.
U.S. Appl. No. 11/097,947, Non-Final Rejection Nov. 10, 2009.
U.S. Appl. No. 11/097,947, Final Rejection Jun. 7, 2010.
U.S. Appl. No. 11/097,947, Response to Office Action Mar. 10, 2010.
U.S. Appl. No. 10/818,574, filed Apr. 6, 2004.
U.S. Appl. No. 10/818,574, Non-Final Rejection Feb. 4, 2009.
U.S. Appl. No. 10/818,574, Response to Office Action May 4, 2009.
U.S. Appl. No. 11/074,453, filed Mar. 8, 2005.
U.S. Appl. No. 11/074,453, Non-Final Rejection Mar. 4, 2009.
U.S. Appl. No. 11/074,453, Requirement for Election Mar. 31, 2010.
U.S. Appl. No. 11/074,453, Notice of Non-compliant response Nov. 9, 2009.
U.S. Appl. No. 11/074,453, Response to Office Action Apr. 29, 2010.
U.S. Appl. No. 11/074,453, Response to Office Action Nov. 23, 2009.
U.S. Appl. No. 11/074,453, Response to Office Action Jul. 6, 2009.
U.S. Appl. No. 11/794,830, filed Jan. 22, 2008.
U.S. Appl. No. 11/794,830, Final Rejection Dec. 7, 2009.
U.S. Appl. No. 11/794,830, Non-Final Rejection May 27, 2009.
U.S. Appl. No. 11/794,830, Response to Office Action Sep. 28, 2009.
U.S. Appl. No. 11/794,830, Response to Office Action Apr. 7, 2010.
U.S. Appl. No. 11/903,607, filed Sep. 24, 2007.
U.S. Appl. No. 11/903,607, Final Rejection Jan. 28, 2010.
U.S. Appl. No. 11/903,607, Non-Final Rejection May 13, 2009.
U.S. Appl. No. 11/903,607, Response to Office Action Aug. 12, 2009.
U.S. Appl. No. 11/903,607, Response to Office Action Apr. 28, 2010.
U.S. Appl. No. 12/442,549, filed Mar. 24, 2009.
U.S. Appl. No. 12/477,179, filed Jun. 3, 2009.
U.S. Appl. No. 12/477,208, filed Jun. 3, 2009.
U.S. Appl. No. 12/477,213, filed Jun. 3, 2009.
U.S. Appl. No. 12/477,225, filed Jun. 3, 2009.
U.S. Appl. No. 12/477,189, filed Jun. 3, 2009.
U.S. Appl. No. 12/721,619, filed Mar. 11, 2010.
U.S. Appl. No. 11/715,181, filed Mar. 7, 2007.
U.S. Appl. No. 11/715,181, Non-Final Rejection Nov. 3, 2009.
U.S. Appl. No. 11/715,181, Non-Final Rejection May 12, 2010.
U.S. Appl. No. 11/715,181, Response to Office Action Feb. 3, 2010.
International Search Report for PCT/IB05/003842 filed Dec. 21, 2005 (WO2006/072822).
Written Opinion for PCT/IB05/003842 filed Dec. 21, 2005 (WO2006/072822).
International Preliminary Report on Patentability for PCT/IB05/003842 filed Dec. 21, 2005 (WO2006/072822).
International Search Report for PCT/IB07/051945 filed May 23, 2007 (WO2007/141695).
Written Opinion for PCT/IB07/051945 filed May 23, 2007 (WO2007/141695).
International Preliminary Report on Patentability for PCT/IB07/051945 filed May 23, 2007 (WO2007/141695).
International Search Report for PCT/IB07/051946 filed May 23, 2007 (WO2007/141696).
Written Opinion for PCT/IB07/051946 filed May 23, 2007 (WO2007/141696).

International Preliminary Report on Patentability for PCT/IB07/051946 filed May 23, 2007 (WO2007/141696).
International Search Report for PCT/IB07/051947 filed May 23, 2007 (WO2007/141697).
Written Opinion for PCT/IB07/051947 filed May 23, 2007 (WO2007/141697).
International Preliminary Report on Patentability for PCT/IB07/051947 filed May 23, 2007 (WO2007/141697).
International Search Report published Apr. 23, 2009 for PCT/IB071051948 filed May 23, 2007 (WO2007/141698).
Written Opinion published Mar. 13, 2009 PCT/IB07/051948 filed May 23, 2007 (WO2007/141698).
International Preliminary Report on Patentability published Mar. 17, 2009 for PCT/IB07/051948 filed May 23, 2007 (WO2007/141698).
International Search Report for PCT/IB07/053906 filed Sep. 26, 2007 (WO2008/038232).
Written Opinion for PCT/IB07/053906 filed Sep. 26, 2007 (WO2008/038232).
International Preliminary Report on Patentability for PCT/IB07/053906 filed Sep. 26, 2007 (WO2008/038232).
International Search Report for PCT/IB01/01406 filed Aug. 8, 2001 (WO2002/013438).
International Preliminary Report on Patentability for PCT/IB01/01406 filed Aug. 8, 2001 (WO2002/013438).
International Search Report for PCT/IB2007/053760 filed Sep. 18, 2007 (WO2008/035280).
Written Opinion for PCT/IB2007/053760 filed Sep. 18, 2007 (WO2008/035280).
International Preliminary Report on Patentability for PCT/IB2007/053760 filed Sep. 18, 2007 (WO2008/035280).
Rintelman, Mary Jane, "Choice and cost-savings", Credit Union Management, vol. 19, No. 7, pp. 48, 50. Jul. 1996.
Woodard, Kathy, "stay healthy for real fun - and profit", Business First Columbus, vol. 12, No. 19, S.1, p. 13. Jan. 1996.
Spencer, Peter L., "New plan cuts health car costs in half (advantage of health care plan with high deductible)", Consumers' Research Magazine, vol. 76, No. 10, pp. 16. Oct. 1993.
Communuity Hearth Health Programs: Components, Ratio: John P. Elder, Thomas L. Schmid, Phyillis Dower and Sonja Hedlund; Journal of Public Health Policy; Palgrave Macmillian; 1993 winter; pp. 463-479.
Ferling ("New plans, New policies," Ferling, Rhona. Best's Review; Apr. 1993 p. 78).
"Plan Highlights for El Paso ISD" Salary Protection Insurance Plan, web-site - http://w3.unumprovident.com/enroll/elpasoisd/your_plan.htm, Mar. 3, 2008.
Consumer-Driven Health Plans Catch on as Myths Fall by Wayside (Sep. 4). PR Newswire, 1.
Art Technology Group; Discovery Holdings to exploit online interest in healthcare and life assurance with ATG commerce functionality; Revenue potential significant as 70% of Discovery members access the internet. (Oct. 28). M2 Presswire, 1.
"Absenteeism Control"; Cole, Thomas C. et al; Management Decision; London: 1992. vol. 20, Iss. 2; p. 12 (AC).
Saleem, Haneefa: "Health Spending Accounts"; Dec. 19, 2003; posted online at http://www.bls.gov/opub/cwc/print/cm20031022ar01p1.htm.
Insure.com; "The lowdown on life insurance medical exams"; Jun. 28, 2006; Imaged from the Internet Archive Waybackmachine on May 10, 2006 at http://web.archive.org/web/20060628231712/http://articles.moneycentral.msn.com/Insurance/Insureyourlife/thelowdownonlifeinsurancwemedicalexams.aspx.
definition of insurance, New Penguin Business Dictionary, Retreieved Oct. 26, 2008 from http://www.credoreference.com/entry/6892512/.

Andrew Cohen; Putting Wellness to work; date Mar. 1, 1997; Athletic Business, pp. 1-7.
www.netpulse.net; Netpulsue Makes Working Out More than a Calorie-Burning Session; date Mar. 21, 1998, pp. 1-2,.
www.netpulse.net; 24 Hour Fitness Partners with Netpulse; date Mar. 9, 1998; p. 1.
Trends in Medical Benefit Plan Design to Control Claim Costs; Record of Society of Actuaries; date 1982; vol. 8, No. 2, pp. 515-531.
David Richards, Return of Premium Disability Insurance; The Black Hole, dated Jul. 15, 2010, p. 1-4 .
002 Co-pending U.S. Appl. No. 09/876,311, Non-final Office Action mailed Jul. 9, 2010.
019 Co-pending U.S. Appl. No. 11/074,453, Final Office Action mailed Jul. 19, 2010.
015 Co-pending U.S. Appl. No. 11/189,647, Request for Continued Examination filed Jul. 19, 2010.
021 Co-pending U.S. Appl. No. 11/715,181, Response filed Aug. 12, 2010.
003-1 Co-pending U.S. Appl. No. 12/112,165, Non-final Office Action mailed Sep. 2, 2010.
U.S. Appl. No. 09/876,311, Response to Office Action Feb. 5, 2009.
U.S. Appl. No. 09/876,311, Response to Office Action May 28, 2009.
U.S. Appl. No. 09/876,311, Response to Office Action Sep. 10, 2009.
U.S. Appl. No. 09/876,311, Response to Office Action May 17, 2010.
U.S. Appl. No. 09/982,274.
U.S. Appl. No. 09/982,274, Final Rejection Nov. 27, 2006.
U.S. Appl. No. 09/982,274, Final Rejection May 6, 2008.
U.S. Appl. No. 09/982,274, Final Rejection Jun. 9, 2009.
U.S. Appl. No. 09/982,274, Non-Final Rejection Mar. 3, 2006.
U.S. Appl. No. 09/982,274, Non-Final Rejection Aug. 9, 2007.
U.S. Appl. No. 09/982,274, Non-Final Rejection Oct. 17, 2008.
U.S. Appl. No. 09/982,274, Response to Office Action Sep. 6, 2006.
U.S. Appl. No. 09/982,274, Response to Office Action May 29, 2007.
U.S. Appl. No. 09/982,274, Response to Office Action Jan. 22, 2008.
U.S. Appl. No. 09/982,274, Response to Office Action Aug. 6, 2008.
U.S. Appl. No. 09/982,274, Response to Office Action Feb. 17, 2009.
U.S. Appl. No. 09/982,274, Notice of Appeal filed Sep. 9, 2009.
U.S. Appl. No. 09/982,274, Appeal Brief Filed Nov. 9, 2009.
U.S. Appl. No. 09/982,274, Reply Brief filed Apr. 2, 2010.
U.S. Appl. No. 12/112,165.
U.S. Appl. No. 12/122,549.
U.S. Appl. No. 11/198,206.
U.S. Appl. No. 11/198,206, Final Rejection Jan. 23, 2009.
U.S. Appl. No. 11/198,206, Non-Final Rejection Jun. 30, 2008.
U.S. Appl. No. 11/198,206, Response to Office Action Oct. 30, 2008.
U.S. Appl. No. 12/333,465.
U.S. Appl. No. 12/262,266.
U.S. Appl. No. 12/303,388.
U.S. Appl. No. 12/303,391.
U.S. Appl. No. 12/303,395.
U.S. Appl. No. 12/303,399.
U.S. Appl. No. 12/441,447.
U.S. Appl. No. 10/344,176.
U.S. Appl. No. 10/344,176, Final Rejection Oct. 30, 2008.
U.S. Appl. No. 10/344,176, Final Rejection Mar. 2, 2010.
U.S. Appl. No. 10/344,176, Non-Final Rejection Dec. 19, 2007.
U.S. Appl. No. 10/344,176, Non-Final Rejection Jun. 8, 2009.
U.S. Appl. No. 10/344,176, Response to Office Action May 19, 2008.
U.S. Appl. No. 10/344,176, Response to Office Action Mar. 2, 2009.
ISR - PCT/IB05103842-International Search Report for PCT/IB05/003842 filed Dec. 21, 2005 (WO2006/072822).

* cited by examiner

METHOD OF CALCULATING A PREMIUM PAYABLE BY AN INSURED PERSON ON A LIFE INSURANCE POLICY

BACKGROUND OF THE INVENTION

This invention relates to a method of calculating a premium payable by an insured person on a life insurance policy.

Typical life insurance policies include a premium which is either payable monthly or annually. The premium increases by an amount which is typically calculated annually and which is normally related to inflation.

It is an object of the present invention to provide an alternative method of calculating the premium payable

SUMMARY OF THE INVENTION

According to the present invention there is provided a method of calculating a premium payable by an insured person on a life insurance policy, the method comprising the steps of:
  obtaining first information regarding the claims made from a health insurance plan of the insured person;
  obtaining second information regarding the general well-being and/or lifestyle of the insured person; and
  using the first and second information to calculate the amount of the premium payable.

The first information may be the amount of claims made from the health insurance plan.

The second information is preferably obtained by:
  defining a plurality of health related facilities and/or services;
  offering the facilities and/or services to the insured person;
  monitoring the use of the facilities and/or services by the insured person; and
  allocating points to the insured person depending on the use of the facilities and/or services by the insured person, wherein the second information is the amount of points allocated to the insured person.

The plurality of health related facilities and/or services may include at least one of the group consisting of a membership of health clubs, membership of gymnasiums, membership of fitness programmes, weight-loss programmes, programmes to quit smoking and preventive medical procedures.

The premium payable is typically calculated at least annually.

The annual calculation is preferably comprised of two components, a first component being a pre-agreed increase and a second component being a further increase or decrease determined by the first and second information.

The annual calculation may have a pre-agreed maximum amount, which maximum amount is related to other life insurance products available.

DETAILED DESCRIPTION OF THE INVENTION

The method of calculating a premium payable by an insured person on a life insurance policy according to the present invention is aimed at encouraging the insured person to adopt a healthy lifestyle.

Life insurance policies are well known where an insured person pays a premium, typically a monthly premium, to an insurance company. If the insured person dies, the insurance company pays out a pre-agreed amount to the beneficiaries of the life insurance policy.

These insurance policies are normally straightforward and the monthly premium is calculated based on the amount of insurance that the insured person has purchased. The premium is then recalculated annually to take such factors as inflation and automatic annual benefit increases into account.

The present invention seeks to calculate the premiums payable by the insured person in a different manner which is aimed at encouraging the insured person to adopt a healthy lifestyle. This healthy lifestyle manifests in improved mortality which can be passed on to the insured person as a premium reduction.

Accordingly, different criteria are introduced, and the premium payable is calculated based on these criteria. The criteria used are as follows.

First information is obtained from the insured person regarding the claims made to a health insurance plan of the insured person. The health insurance plan may be a traditional indemnity health insurance plan of the insured person or may be another type of health insurance plan.

It is envisaged that the present invention will be more easily implemented where the life insurers are somehow associated with the health insurers in order to facilitate the ease of transfer of information. However, it will be appreciated that this is not essential for the present invention.

The first information preferably more specifically relates to the amount of claims that the insured person has made from their health insurance plan. As will be explained below in more detail, the premium payable on the life insurance policy will be calculated to be relatively higher if the amount of claims made from the health insurance plan is relatively higher. The premium payable on the life insurance policy will be calculated to be relatively lower if the amount of claims made from the health insurance plan is relatively lower. In actuarial terms, this means that the premium can be priced on "Select" mortality rates for a longer duration than traditional pricing, before moving to "Ultimate" mortality rates.

Second information is obtained regarding the general well-being and/or lifestyle of the insured person. The general well-being and/or lifestyle of the insured person is measured by defining a plurality of health related facilities and/or services and offering the facilities and/or services to the insured person for use.

The facilities and/or services include any of a membership of a health club, membership of gymnasiums, membership of fitness programmes, weight-loss programmes, programmes to quit smoking and preventive medical procedures.

It will be appreciated that the use of any of the above will have a positive effect on the insured person's health. Therefore, the use of the facilities and/or services is monitored and points are allocated to the insured person depending on the use of the facilities and/or services.

The second information regarding the general well-being and/or lifestyle of the insured person is in the form of these allocated points. A higher points allocation indicates that the insured person is taking steps to maintain their health and this is essentially rewarded when the premium on the life insurance policy is calculated. The higher the allocated points are, the lower the calculated premium payable will be.

The above will now be described in more detail referring specifically to the implementation of the present invention by the patentee.

The patentee presently manages a traditional indemnity health insurance plan together with their so-called Vitality programme. The Vitality programme is described in more detail in U.S. patent application Ser. No. 09/265,240, the contents of which are incorporated herein by reference.

In short, the Vitality programme rewards members for utilising approved health related facilities and/or services. For example, members are rewarded for utilising gymnasiums, Smoke Enders™ and Weighless™.

Members are rewarded by a points allocation system and depending on the total number of points allocated to a member, they fall within one of four categories. In the implementation of the Vitality programme, these categories have been named blue, bronze, silver and gold. All members are placed initially in the blue class and only once a member has accumulated a number of points is their Vitality status upgraded to the next appropriate class.

The Vitality status of the member is used when calculating the premium payable by the member on a life insurance policy.

A personal health matrix is set up for each insured person whereby the Vitality status is used in conjunction with the amount of claims made by the insured person to calculate the premium payable on the life insurance policy.

Premiums on life insurance policies are typically recalculated annually, and this will be used for illustrative purposes in the present invention. However, it will be appreciated that this time period can be adjusted.

The annual recalculation or adjustment includes a pre-agreed base percentage increase amount which is typically linked to inflation. For example, the automatic annual premium increase may be 10%.

The personal health matrix is then used to calculate the premium payable by either increasing or decreasing this 10%.

If the insured person has a high Vitality status and their claims have been low, the 10% will be decreased.

By way of example, the prototype of the present invention has been implemented using 4 different matrices that may be applied. The factors that determine the matrix to be applied are as follows:

Is there more than one life insured on the life plan? If yes, then the family matrix is applied. If no, then the principal matrix is applied.

Is the policyholder on a core or comprehensive health insurance plan? The grids differ by health plan as the various health plans provide different benefits, which lead to different claim bands.

| Family Core plan | | | | |
|---|---|---|---|---|
| | Vitality | | | |
| Claims | Blue | Bronze | Silver | Gold |
| 0 to 1500 | 0.00% | 0.00% | −0.25% | −1.00% |
| 1501 to 3000 | 1.45% | 1.20% | 0.45% | −0.75% |
| 3001 to 6000 | 1.90% | 1.70% | 1.00% | −0.50% |
| 6001 to 10000 | 2.55% | 2.25% | 1.50% | −0.25% |
| 10001 to 15000 | 3.15% | 2.80% | 2.00% | 0.00% |
| 15001 to 25000 | 3.65% | 3.35% | 2.50% | 0.25% |
| 25001 + | 3.90% | 3.55% | 2.80% | 0.75% |

| Family Comprehensive plan | | | | |
|---|---|---|---|---|
| | Vitality | | | |
| Claims | Blue | Bronze | Silver | Gold |
| 0 to 3000 | 0.00% | 0.00% | −0.50% | −2.00% |
| 3001 to 5000 | 1.35% | 1.00% | 0.00% | −1.00% |
| 5001 to 10000 | 2.10% | 1.85% | 1.00% | −0.50% |
| 10001 to 15000 | 2.80% | 2.30% | 1.50% | 0.00% |
| 15001 to 25000 | 3.30% | 3.00% | 2.10% | 0.25% |
| 25001 to 35000 | 3.65% | 3.30% | 2.50% | 0.50% |
| 35001 + | 3.90% | 3.70% | 2.95% | 0.75% |

| Principal only Core plan | | | | |
|---|---|---|---|---|
| | Vitality | | | |
| Claims | Blue | Bronze | Silver | Gold |
| 0 to 1000 | 0.00% | 0.00% | −0.25% | −1.00% |
| 1001 to 2000 | 1.45% | 1.20% | 0.45% | −0.75% |
| 2001 to 3500 | 1.90% | 1.70% | 1.00% | −0.50% |
| 3501 to 5000 | 2.55% | 2.25% | 1.50% | −0.25% |
| 5001 to 10000 | 3.15% | 2.80% | 2.00% | 0.00% |
| 10001 to 15000 | 3.65% | 3.35% | 2.50% | 0.25% |
| 15001 + | 3.90% | 3.55% | 2.80% | 0.75% |

| Principal only Comprehensive plan | | | | |
|---|---|---|---|---|
| | Vitality | | | |
| Claims | Blue | Bronze | Silver | Gold |
| 0 to 2000 | 0.00% | 0.00% | −0.50% | −2.00% |
| 2001 to 3500 | 1.35% | 1.00% | 0.00% | −1.00% |
| 3501 to 5000 | 2.10% | 1.85% | 1.00% | −0.50% |
| 5001 to 10000 | 2.80% | 2.30% | 1.50% | 0.00% |
| 10001 to 15000 | 3.30% | 3.00% | 2.10% | 0.25% |
| 15001 to 25000 | 3.65% | 3.30% | 2.50% | 0.50% |
| 25000 + | 3.90% | 3.70% | 2.95% | 0.75% |

As can be seen from the above matrices, the amount of health claims and Vitality status determine the annual additional percentage increase or decrease to premiums. Clearly, there are cases where premium reductions occur, e.g., a Gold Vitality member.

Claims taken into account include Chronic medication, In Hospital Benefits, Insured Procedure Benefits and day to day expenditure. This expenditure may apply to all lives or a subset of lives on the health plan. As can be seen from these matrices, there is an initial band of claims which do not translate into any increases of premium on the life plan.

The bands of the matrix will be altered annually to allow for medical inflation. This prevents policyholders getting higher increases in their life premiums as medication and procedures increase annually with inflation.

One may also impose levels of protection, to ensure that however bad the clients health is, their premiums are still sustainable for long periods of time. For example, one could guarantee that premiums do not exceed the premiums one would have paid on a standard life plan for 5 years, and do not exceed 110% of this premium from years 6 to 10, 115% from years 11-15 and 120% for the remainder of the policy term. This provides piece of mind that the plan is sustainable no matter how bad health is.

Thus it will be appreciated that the premiums on the life insurance policy may increase or decrease annually on the policy anniversary by an additional percentage depending on the amount of claims on the health plan as well as the Vitality status.

The calculation of the premium payable encourages the insured person to look after their health which obviously has benefits for the insured person but also helps the insurer by minimising their risk.

We claim:

1. A method of calculating a premium payable by an insured person on a life insurance policy, the method comprising:

obtaining, by an information processing system, first information regarding any claims made from a health insurance plan of the insured person;

obtaining, by the information processing system, second information regarding a general well-being and/or lifestyle of the insured person by:

defining a plurality of health related facilities and/or services;

offering the facilities and/or services to the insured person;

monitoring a use of the facilities and/or services by the insured person;

allocating points to the insured person depending on the use of at least one facility and/or service in the plurality of health related facilities and/or services by the insured person; and assigning, by the information processing system, a wellness program status category to the insured person based on the points that have been allocated to the insured person, wherein the second information is the wellness program status category assigned to the insured person, and wherein the wellness program status category indicates a participation level of the insured person within a wellness program;

using, by the information processing system, the first information in combination with the second information to calculate an amount of the premium payable; and re-calculating, by the information processing system, the amount of the premium payable using updated first and second information at least annually, wherein the re-calculating the amount of the premium payable using updated first and second information at least annually is comprised of two components: a first component being a pre-agreed premium increase and a second component being a further increase or decrease of the pre-agreed premium increase determined by the first and second information, wherein the re-calculating the amount of the premium payable using updated first and second information at least annually has a pre-agreed maximum amount, and wherein the pre-agreed premium increase and the pre-agreed maximum amount is between the insured person and an insurance company.

2. The method according to claim 1, wherein the first information is the amount of claims made from the health insurance plan.

3. The method according to claim 1, wherein the plurality of health related facilities and/or services includes at least one of the group consisting of a membership of health clubs, membership of gymnasiums, membership of fitness programs, weight-loss programs, programs to quit smoking and preventive medical procedures.

4. The method according to claim 1, wherein the pre-agreed maximum amount is related to other life insurance products available from the insurance company.

5. The method according to claim 1, wherein the re-calculating the amount of the premium payable using updated first and second information at least annually is comprised of two components, a first component being a pre-agreed premium increase and a second component being a further increase of the pre-agreed premium increase determined by the first and second information, wherein the pre-agreed premium increase is between the insured person and an insurance company.

6. The method according to claim 1, wherein the re-calculating the amount of the premium payable using updated first and second information at least annually is comprised of two components, a first component being a pre-agreed premium increase and a second component being a further decrease of the pre-agreed premium increase determined by the first and second information, wherein the pre-agreed premium increase is between the insured person and an insurance company.

7. The method according to claim 1, wherein the pre-agreed maximum amount is based on premiums associated with a standard life insurance policy over a given period of time, wherein the pre-agreed maximum amount is one of equal to and below the premiums.

8. The method according to claim 1, wherein the pre-agreed maximum amount is based on premiums associated with a standard life insurance policy, wherein the pre-agreed maximum set to one of equal to and below the premiums for a first given period of time and is set to a given percentage above the premiums for at least a second given period of time.

* * * * *